Figure 1:
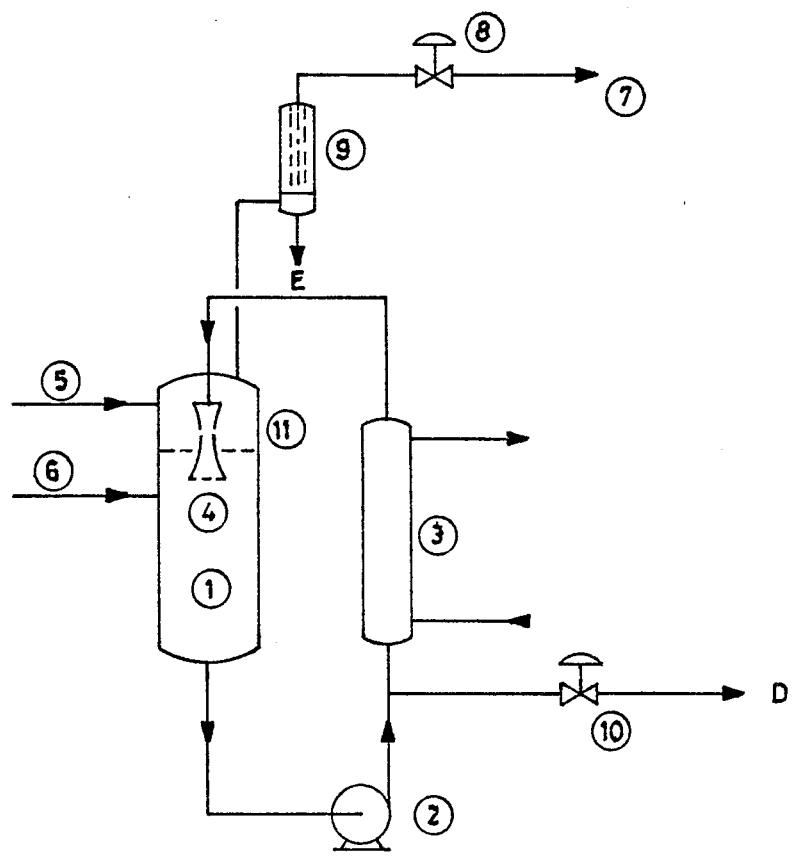

United States Patent [19]

Couteau et al.

[11] 4,098,820
[45] Jul. 4, 1978

[54] PROCESS FOR THE PRODUCTION OF FORMAMIDES

[75] Inventors: Willy Couteau, Brussels; Jean Ramioulle, Bierghes, both of Belgium

[73] Assignee: UCB, Societe Anonyme, Brussels, Belgium

[21] Appl. No.: 776,370

[22] Filed: Mar. 10, 1977

[30] Foreign Application Priority Data

Mar. 12, 1976 [GB] United Kingdom ............... 10027/76

[51] Int. Cl.² .......................................... C07C 102/00
[52] U.S. Cl. ............................. 260/561 R; 261/36 R; 261/DIG. 75
[58] Field of Search ..................... 261/DIG. 75, 36 R; 260/561 R, 561

[56] References Cited

U.S. PATENT DOCUMENTS

| 3,503,593 | 3/1970 | Nelson | 261/36 R |
| 3,928,199 | 12/1975 | Kirk et al. | 261/DIG. 75 |
| 3,947,359 | 3/1976 | Laurie | 261/DIG. 75 |
| 4,017,565 | 4/1977 | Müller | 261/DIG. 75 |
| 4,018,859 | 4/1977 | Müller | 261/DIG. 75 |

FOREIGN PATENT DOCUMENTS 1,213,173  11/1970  United Kingdom.

Primary Examiner—Arthur P. Demers
Attorney, Agent, or Firm—Wenderoth, Lind & Ponack

[57] ABSTRACT

The invention relates to an improved process for the production of a formamide, wherein a current of a gas containing carbon monoxide is reacted at elevated temperature (50°–200° C) and pressure (5–110 bars) in a reaction zone with a recycled current of liquid reaction mixture containing (a) a nitrogen-containing compound selected from the group consisting of ammonia, a primary alkylamine and a secondary alkylamine (e.g. monomethylamine or dimethylamine);
(b) a methanolic solution of an alkali metal or earth metal methoxide as catalyst, and
(c) the formamide produced as reaction product, part of the current of liquid reaction mixture being withdrawn in order to recover the formamide therefrom.

The characteristic feature of the invention consists in that the recycled liquid reaction mixture is used for sucking and dispersing the current of gas in the reaction zone. Advantages of the process are: excellent heat exchange, high productivity and yield, absence of solid deposits on the internal surfaces of the apparatus, lower operating pressures and temperatures, use of apparatus of smaller dimensions, suppression of recycling of carbon monoxide, continuous operation etc.

16 Claims, 2 Drawing Figures

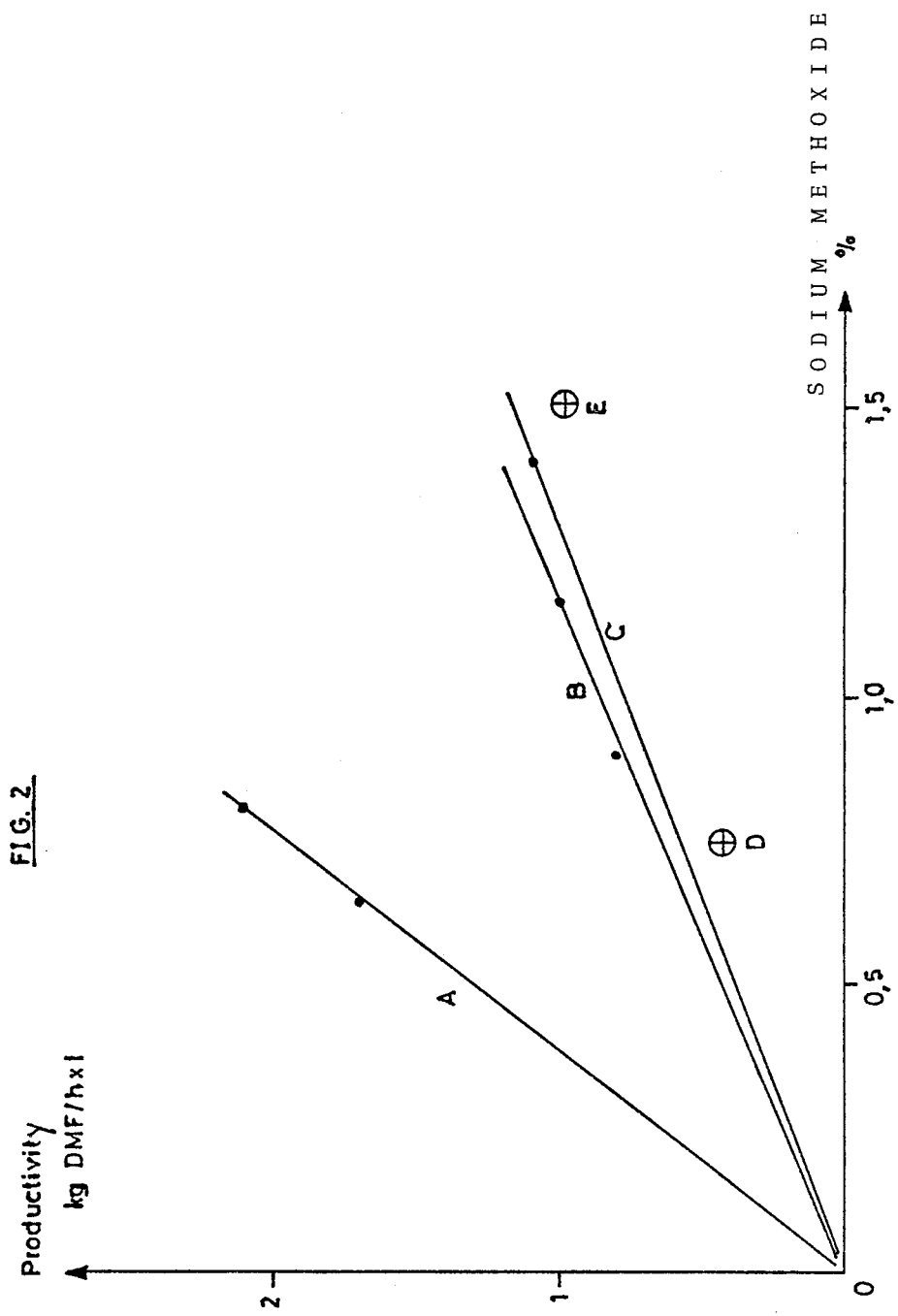

PROCESS FOR THE PRODUCTION OF FORMAMIDES

The present invention relates to a new process for the production of formamides, wherein carbon monoxide is reacted under pressure and at elevated temperature with ammonia or a primary or secondary alkylamine in the presence of a methanolic solution of an alkali metal or alkaline earth metal methoxide as catalyst.

Various processes are already known for the production of formamide and alkyl-substituted formamides; these are, in particular, described in Ullmann's "Encyklopädie der technischen Chemie," 3rd edition, 1956, volume 7, pages 672–678. Of these processes, the most interesting, from the commercial point of view, are those which start with carbon monoxide and ammonia or an alkylamine (in view of the low cost and ease of obtaining these starting materials) and in which the catalyst used is a methanolic solution of an alkali metal or alkaline earth metal methoxide and preferably of sodium methoxide.

However, in the production of formamides by this method, a number of technical difficulties are encountered which hitherto it has been possible to overcome more or less successfully. A first difficulty is that this reaction has a pronounced exothermic character: about 27 Kcal are generated per mole of dimethylformamide formed in the synthesis from carbon monoxide and dimethylamine; it is, therefore, imperative to use very efficient heat exchange means if it is desired to dissipate the heat of reaction correctly. A second difficulty is that the alkali metal or alkaline earth metal methoxide used as catalyst, which has a good solubility in methanol, has, on the other hand, only a poor solubility in the formamides formed by the reaction, as is shown in the following Table 1 which relates to dimethylformamide (DMF):

TABLE 1

| Solubility of sodium methoxide in the system DMF/CH$_3$OH at ambient temperature (% by weight) | | |
|---|---|---|
| DMF | CH$_3$OH | CH$_3$ONa |
| 100 | 0 | 0.06 |
| 99 | 1 | 0.72 |
| 90 | 10 | 4.46 |

| DMF | CH$_3$OH | CH$_3$ONa |
|---|---|---|
| 80 | 20 | 10.67 |
| 60 | 40 | >14.7 |
| 40 | 60 | >20.6 |
| 20 | 80 | >25.6 |

The result of this is that, in the course of time, deposits of a solid precipitate of catalyst are formed, giving rise to clogging of pipes and valves in the installation and also solid incrustations on the heat exchange surfaces, with the result that heat exchange becomes increasingly poor in the course of time. A third difficulty is that, in the presence of humidity, the alkali metal or alkaline earth metal methoxide reacts with carbon monoxide to form the corresponding alkali metal or alkaline earth metal formate, which is also very sparingly soluble in the reaction mixture and, consequently, also gives rise to the same operational disturbances as mentioned above in connection with the alkali metal or alkaline earth metal methoxide, as will be shown in the following Table 2 which relates to dimethylformamide:

TABLE 2

| Solubility in % by weight of sodium formate in the system DMF/CH$_3$OH at ambient temperature | | |
|---|---|---|
| DMF | CH$_3$OH | HCOONa |
| 100 | 0 | 0 |
| 80 | 20 | 0.36 |
| 60 | 40 | 1.07 |
| 20 | 80 | 2.77 |
| 0 | 100 | 3.33 |

Furthermore, there is a progressive reduction of the activity of the catalyst because of its conversion into alkali metal or alkaline earth metal formate, which does not catalyse the conversion of ammonia and/or amines and carbon monoxide into the corresponding formamides. In addition, this synthesis is still carried out at the present time under conditions of relatively high temperature and pressure, which it would be advantageous to lower in order to reduce not only investment expenses involved but also the operating costs.

Japanese Patent Specification No. 306,134 describes a process in which the reaction mixture is circulated between a reactor and a heat exchanger, the circulating means comprising a venturi nozzle into which carbon monoxide is injected under pressure as carrier for the liquid reaction mixture. By means of this process, it is possible to dissipate efficiently the heat of reaction; nevertheless, in the course of time, a catalyst precipitate is formed which progressively reduces the flow rate of the reaction mixture in the pipes and also the heat exchange between the reaction mixture and the cooling surface of the heat exchanger. Furthermore, the dispersion of the gas bubbles in the liquid medium is relatively coarse, which entails an insufficient contact surface area between gas and liquid.

For this reason, the patentee of this Japanese Patent Specification No. 306,134 subsequently describes in British Patent Specification No. 1,213,173 a process in which it is proposed to meet the drawbacks indicated above. This process comprises inserting a liquid circulation pump in the reactor-heat exchanger circuit described in Japanese Patent Specification No. 306,134. The liquid mixture is delivered by the pump to the venturi nozzle at a flow rate which is at least 50% higher than the flow rate at which, at atmospheric pressure, the liquid mixture would be sucked by the sole suction force of the gas jet. Consequently, there is a better distribution of the gas bubbles, as well as a reduction of their dimensions, which ensures better contact between the liquid phase and the gas phase. Furthermore, solid deposits of catalyst tend to be deposited to a lesser extent because of the turbulent flow caused by the pump. Nevertheless, this process still has considerable disadvantages on a technical scale.

First, mention is to be made of the need to recycle the unreacted carbon monoxide. Before being reintroduced into the reactor, the residual carbon monoxide effluent must be freed from the volatile constituents which it has entrained and then it must be recompressed before being mixed with fresh carbon monoxide fed into the reactor, which involves considerable additional investment expense, practically doubling the cost of the installation. Furthermore, the energy consumed by the recycling compressor is considerable. To this must also again be added the additional cost of the installation and operation of the liquid pump.

Secondly, productivity is not optimum, the term "productivity" being understood to mean the quantity of formamide(s) produced per hour per liter of capacity of the apparatus.

Thirdly, the temperature and pressure conditions are relatively high.

It is for these reasons that for the synthesis of formamide(s) from carbon monoxide and ammonia (or a primary or secondary alkylamine), in the presence of an alkali metal or alkaline earth metal methoxide as catalyst, we have carried out research to develop a process which would be free from the disadvantages of the hitherto known processes, particularly those described in Japanese Patent Specification No. 306,134 and British Patent Specification No. 1,213,173. We have achieved this by the process described hereinafter, which constitutes the subject of the present invention.

Thus the present invention provides an improved process for the production of a formamide, wherein a current of gas containing carbon monoxide is reacted at elevated temperature and pressure in a reaction zone with a recycled current of liquid reaction mixture containing:

(a) a nitrogen-containing compound selected from the group consisting of ammonia, a primary alkylamine and a secondary alkylamine, (b) a methanolic solution of an alkali metal or alkaline earth metal methoxide as catalyst, and (c) the formamide produced as reaction product, part of the current of liquid reaction mixture being withdrawn in order to recover the formamide therefrom and wherein the recycled current of liquid reaction mixture is used for sucking and dispersing the current of gas in the reaction zone.

The process of the present invention can be carried out in any apparatus, provided that the recycled current of liquid reaction mixture is used for sucking and dispersing the current of gas in the reaction zone. However, it is preferable to use an apparatus comprising a reaction vessel, a pump for recycling the current of liquid reaction mixture, a heat exchanger and a means for sucking and dispersing a current of gas in the current of liquid reaction mixture, such as described hereinafter.

Thus, unlike the processes described in the Patent Specifications mentioned above, the carbon monoxide is not the agent entraining the liquid reaction medium but, on the contrary, the liquid reaction medium is the agent entraining carbon monoxide or gaseous current containing it. From the industrial point of view, this difference in operation has considerable repercussions on the economy of the process because, in the process of the present invention, it is not necessary to recycle carbon monoxide, so that it is thus possible to eliminate the considerable costs for investment and operation, mention of which has already been made above.

Furthermore, productivity is considerably improved, while operating under far more moderate conditions of temperature and pressure than those recommended in the two above-mentioned Patent Specifications and while, nevertheless, obtaining a practically quantitative yield of reaction product. Furthermore, the process of the present invention can easily be carried out continuously.

In order to enable the characteristic features of the process of the present invention to be better understood, an apparatus which can be used for this purpose will first be described with reference to FIG. 1 of the accompanying drawings.

The apparatus comprises a reaction vessel 1, a circulation pump 2, a heat exchanger 3 and a device 4 for sucking and dispersing carbon monoxide into the liquid reaction mixture which permanently circulates between the reaction vessel 1 and the heat exchanger 3 through the circulation pump 2, in the direction shown by the arrows in FIG. 1. The device 4 can comprise a perforated plate through which pass the fine jets of the liquid reaction mixture which are crashed down on an impact plate so as to form a mist with the gaseous phase in such a manner that intimate contact between the gaseous phase and the liquid phase is achieved. In the accompanying drawing, the device 4 is shown in the form of a venturi; however, it is obvious that the device 4 used may be any device which ensures sucking of the gas phase by means of the liquid phase and produces the most intimate possible mixing together of these two phases.

The carbon monoxide (or gas containing it) is introduced at a constant flow rate through pipe 5 into the top part of the vessel 1, which is reserved for the gaseous phase, while the ammonia or the primary or secondary amine, which contains the appropriate amount (specified hereinafter) of an alkali metal or alkaline earth metal methoxide dissolved in methanol, is fed at a constant flow rate through pipe 6 below the level of separation 11 between the gaseous phase and the liquid phase. If desired, the nitrogen-containing compound and the catalyst may also be introduced separately (not shown). The outgoing gases (mainly inert gases and to a considerably lesser extent, small amounts of carbon monoxide) leave the vessel 1 through pipe 7. The pressure in the apparatus is kept constant by introducing the reactants at a constant flow rate and by means of valve 8 which is set at the desired reaction pressure. A condenser 9 retains any products which may be entrained by the inert outgoing gases; this condenser is useful only in cases where very dilute carbon monoxide is used. The reaction mixture is withdrawn from the apparatus through valve 10 set at the level of the liquid reaction mixture 11 in the reaction vessel 1; the amount of reaction mixture withdrawn from the system is thus, at any moment, proportional to the amounts of reactants introduced.

In order to prevent the dispersed gaseous phase which is not dissolved in the reaction medium from being entrained through the pump 2, which would cause damage due to cavitation, it is necessary to provide a reaction vessel the height of which is sufficiently great to ensure that undissolved gas bubbles can return, due to the difference of density, to separation level 11 between the gaseous phase and the liquid phase and, consequently, without being entrained by the pump 2, into the liquid phase circuit.

The flow rate of the pump must be sufficiently high to ensure good heat exchange between the reaction vessel 1 and the heat exchanger 3 so that, in the reaction vessel, there will constantly be a temperature of from about 50° to about 200° C. and preferably of from about 60° to about 100° C., and to establish a contact surface area between the gaseous phase and the liquid phase of 750 to 5,000 square meters per cubic meter and preferably of 1,000 to 2,000 square meters per cubic meter of liquid phase.

In the exchanger 3, the heat exchange between the liquid reaction mixture and the heating and/or cooling liquid is effected indirectly through a heat exchange surface.

The pressure prevailing in the system during the performance of the process of the present invention is between 5 and 110 bars and preferably between 10 and 25 bars. It is clear that it is possible to work at higher pressures but, doing so, one of the advantages of the process according to the invention is lost.

The carbon monoxide used in the process of the present invention may be pure carbon monoxide or a gas containing carbon monoxide and gases which are inert under the conditions of the process, for example hydrogen, nitrogen and hydrocarbons. Thus, the carbon monoxide content in the gas containing carbon monoxide can be from about 20 to 100% by volume and preferably from 50 to 100% by volume. Particular care should be taken to ensure that the gas containing carbon monoxide, contains the smallest possible amount of water, for example less than 5 ppm, since water destroys the catalyst by forming a precipitate of alkali metal or alkaline earth metal formate.

The ammonia used for preparing the formamide (non-alkyl-substituted) according to the process of the present invention may be of technical quality, such as is supplied in liquid form under pressure in cylinders. It may be introduced into the reaction vessel in the gaseous state but is preferably introduced in the liquid state. The water content of the ammonia must also be as low as possible, for the reasons given above, and is, for example, below 5 ppm.

In principle, there is no objection to the use, in the process according to the present invention, of monoalkylamines and dialkylamines the alkyl radical of which contains any number of carbon atoms. However, from a commercial point of view, the mono- and dialkylamines containing 1 or 2 carbon atoms in each alkyl radical are the most interesting, particularly mono- and dimethylamine, which, by the process of the present invention, make it possible to obtain monomethylformamide and dimethylformamide respectively. The alkylamines used in the process of the present invention may be products of normal commercial quality but, as already pointed out above, care must be taken that their water content is as low as possible, for example below 100 ppm.

The molar ratio of carbon monoxide to the nitrogen-containing compound in the process of the present invention is advantageously from 0.2 to 2.0 and preferably from 0.2 to 1.0 if it is desired to produce only formamide (optionally alkyl-substituted). It should, however, be noted that the methanol used to dissolve the alkali metal or alkaline earth metal methoxide may react with the carbon monoxide, forming methyl formate. Consequently, in an alternative mode of operation, it is also possible to work the process of the present invention so as to obtain a reaction product which contains simultaneously formamide (optionally alkyl-substituted) and a variable amount of methyl formate. For this purpose, an amount of carbon monoxide will be used which is in excess over the stoichiometrical amount of nitrogen-containing compound and the greater the amount of methanol used the higher will be the methyl formate content of the reaction product (see Example 5); in this case, the molar ratio of carbon monoxide to nitrogen-containing compound is preferably from 1,0 to 1,4.

The separation of the (optionally alkyl-substituted) formamide from methyl formate in the reaction product is very easily effected by distillation, having regard to the great difference in the boiling points of formamides, methanol and methyl formate:

| | |
|---|---|
| formamide | : 105–6° C./11 mm.Hg. |
| methyl formamide | : 180–185° C./760 mm.Hg. |
| dimethyl formamide | : 153° C./758 mm.Hg. |
| methanol | : 65° C./760 mm.Hg. |
| methyl formate | : 31.5° C/760 mm.Hg. |

The catalyst used in the process of the present invention is an alkali metal or alkaline earth metal methoxide and is preferably sodium methoxide. The catalyst is used in the form of a methanolic solution with a concentration of from 1 to 30% by weight and preferably of from 1 to 5% by weight. The amount of catalyst added (calculated as 100% methoxide) is from about 0.2% to about 4.0% by weight and preferably from about 0.4 to about 2.5% by weight, referred to the amount of nitrogen-containing compound used. The methanolic solution of alkali metal or alkaline earth metal methoxide may be fed separately into the apparatus of the present invention; nevertheless, it is also possible for the catalytic solution to be previously mixed with the ammonia or primary or secondary alkylamine before being fed into the system.

The yields of formamides obtained in the process of the present invention are substantially quantitative; they are practically 100 mol percent, referred to the nitrogen-containing compound and at least 90 mol percent and even at least 95 mol percent, referred to the carbon monoxide, when the latter is technically pure. When using carbon monoxide diluted by inert gases, the yield of the reaction product is dependent upon the partial pressure of the carbon monoxide in the gaseous mixture; the yield increases with an increasing content of carbon monoxide becoming 90 mol percent and even 95 mol percent when the carbon monoxide is technically pure.

One advantageous characteristic feature of the process of the present invention is its great flexibility of operation, which is due, on the one hand, to the excellent heat exchange which permits high productivity and, on the other hand, to the high rate of circulation of the liquid reaction mixture, which not only provides good stability of the reaction temperature and optimum contact between gas phase and liquid phase but also ensures the absence of solid deposits (alkali metal or alkaline earth metal methoxide and/or formate) on the internal surfaces of the apparatus, particularly on the heat exchange surfaces, any solid precipitate which may be formed being kept in suspension in the liquid phase because of the turbulence produced by the pump. The problem of solid deposits encountered in certain known processes is thus radically overcome. Furthermore, depending upon requirements, this operational flexibility makes it possible to use variable amounts of catalyst, variable carbon monoxide pressures, variable reaction temperatures, variable circulation rates of the reaction mixture, simultaneous production of formamides and of methyl formate and so on, this being achieved in one and the same apparatus.

Another advantageous characteristic feature is that the liquid reaction mixture occupies a volume of at least 80% and preferably of at least 90% of the total useful volume of the apparatus, thus making it possible for the cost of construction and installation of the apparatus for a given hourly production to be considerably reduced.

As the specific examples given hereinafter will show, another advantageous charactetistic feature is that the production of formamides can be effected under pressures and at temperatures which are substantially lower than those used in the known processes, while, nevertheless, obtaining higher productivity and yields.

Another advantageous characteristic feature of the process of the present invention, which is a determining factor with regard to productivity and yield of reaction product, is the high value of the contact surface area between the gas phase and the liquid phase. The importance of this contact surface area had already been foreshadowed in British Patent Specification No. 1,213,173 referred to above; however, whereas in this Patent Specification the maximum value of this factor (referred to as "factor a") is 510 square meters per cubic meter of liquid phase (see Table 1 of Example 1, column 5), in the process of the present invention, this value is between 750 and 5,000 square meters per cubic meter of liquid phase and preferably between 1,000 and 2,000 square meters per cubic meter of liquid phase.

As already explained above, another advantageous characteristic feature of the process of the present invention is that the various advantages thus achieved are obtained while avoiding the recycling of carbon monoxide which, in the known processes, entails considerable expense for investment in respect of gas cooling condensers and gas compressors.

Finally, another advantage is that the process can be carried out continuously in a reliable and simple manner.

The type of apparatus preferably used for carrying out the process of the present invention is known per se (see Swiss Patent Specification No. 370,057); it has already been used for the selective hydrogenation of vegetable and animal oils and fats for the purpose of hardening them (see German Patent Specification No. 1,906,448). However, apparatus of this kind has hitherto not been used for the synthesis of formamides by the process of the present invention.

In the following examples, which are given only for the purpose of illustrating the present invention, use is made of an apparatus of the kind illustrated diagrammatically in FIG. 1 of the accompanying drawings, the total useful volume of this apparatus being 60 liters, the pump for circulating the reaction mixture being adjusted to a flow rate providing a contact surface area between the gas phase and the liquid phase of 1200 sq. meters per cubic meter of liquid phase. The volume occupied by the liquid phase in the apparatus is from about 50 to 55 liters, which represents a rate of occupation of from 83 to 91% of the total useful volume of the apparatus.

EXAMPLE 1.

113.2 kg. per hour of a mixture containing 69.65% by weight of dimethylamine, 29.70% by weight of methanol and 0.55% by weight of sodium methoxide (0.79% by weight referred to the dimethylamine) is introduced through pipe 6. 50.9 kg. of carbon monoxide of 99.5% purity are introduced per hour through pipe 5. All these reactants are practically free from water and carbon dioxide. The operating pressure is kept at 22 bars by appropriately adjusting the blow-off 7, while the temperature is kept strictly constant at 90° C. by means of heat exchanger 3, through which water flows at a temperature of 60° C. In order to maintain a constant liquid level at 11, 161.5 kg. of a mixture containing 78% by weight of dimethylformamide are extracted per hour at D, i.e. a production of 126 kg. per hour of 100% dimethylformamide. The yield referred to carbon monoxide is 95 mol percent and the conversion of dimethylamine is 98.5%. The unconverted dimethylamine and the methanol are easily separated from the dimethylformamide by distillation and recycled to the reaction. Under the conditions indicated above, the productivity is 126/60 = 2.1 kg. of dimethylformamide per hour per liter of reactor.

When these results are compared with those of Example 6 of British Patent Specification No. 1,213,173 mentioned above, the following Table is obtained:

| | % of catalyst (by weight) | temperature in ° C. | pressure in bars | productivity (kg/h/liter) |
|---|---|---|---|---|
| According to the present | 0.79 | 90 | 22 | 2.1 |
| According to Example 6 of British Patent Specification No. 1,213,173 | 0.75 | 120 | 20 | 0.43 |

It can be seen that, according to the present invention, although operating substantially at the same pressure and at a considerably lower temperature, productivity is, nevertheless, about 5 times that achieved according to the prior art process.

EXAMPLE 2.

The operation is carried out under the same pressure (22 bars) as in Example 1 but at a still lower temperature, i.e. 70° C. instead of 90° C. 35.2 kg. per hour of a solution containing 69.61% by weight of dimethylamine, 29.86% by weight of methanol and 0.52% by weight of sodium methoxide (0.75% by weight referred to the dimethylamine) on the one hand, and 16.3 kg. per hour of carbon monoxide of 99.2% purity, on the other hand, are introduced. In order to maintain the constant level at 11 in the reactor, 50.2 kg. of a mixture containing 77.7% of dimethylformamide are withdrawn per hour at D. 39 kg. of 100% dimethylformamide are, therefore, produced per hour and the productivity is 0.65 kg. of dimethylformamide per hour per liter of reactor. The yield referred to carbon monoxide is 92 mol percent and the conversion of dimethylamine is 98%.

This Example shows that even at 70° C. (instead of 120° C.) a productivity is obtained which is still higher than that of British Patent Specification No. 1,213,173, i.e. 0.65 kg. instead of 0.43 kg. per hour per liter of reactor.

EXAMPLE 3.

The procedure of Example 1 is followed, but 59.5 kg. of a mixture containing 69.3% by weight of dimethylamine, 29.7% by weight of methanol and 0.1% by weight of sodium methoxide (1.4% by weight referred to the dimethylamine) and also 26.6 kg. of carbon monoxide of 99.5% purity are introduced per hour. The temperature is adjusted to 90° C. and pressure to 10 bars.

84.9 kg. of a mixture containing 77.76% by weight of dimethylformamide are withdrawn per hour at D, i.e. a production of 66 kg. of 100% dimethylformamide per hour.

Therefore, productivity is 66/60 = 1.1 kg. of dimethylformamide per hour per liter of reactor. The yield referred to carbon monoxide is 96 mol percent and the conversion of dimethylamine is 99%.

This Example shows that with far lower carbon monoxide pressures and at lower temperatures than in the prior art process and with a reasonable increase of the catalyst content, by means of the process of the present invention, a much higher productivity is obtained (1.1 instead of 0.43). It will be noted that the favourable result obtained in the present Example is not explained by this slight increase of the catalyst content, as will be demonstrated in the following Examples.

EXAMPLE 4.

In this Example, the effect of the sodium methoxide (catalyst) content on productivity in the process of the present invention and that in the process of British Patent Specification No. 1,213,173 are compared.

The results thus obtained are reproduced in the form of a graph in FIG. 2 of the accompanying drawings, in which curve A represents the productivity of the process of the present invention when carried out at 90° C. and at a pressure of 22 bars; curve B is the productivity of the process of the present invention when carried out at 70° C. and at a pressure of 20 bars; and curve C is that of the process of the present invention when carried out at 90° C. and at a pressure of 10 bars. The point D indicates the result obtained in Example 6 of British Patent Specification No. 1,213,173 at 120° C. and at a pressure of 20 bars and point E indicates the result obtained in Example 4 of British Patent Specification No. 1,213,173 at 120° C. and at a pressure of 50 bars.

This graph clearly shows that whatever the catalyst content, the process of the present invention gives a far higher productivity, while operating under much more moderate conditions of temperature and pressure. It is, in particular, remarkable to note that, for the same productivity of 1.0 kg. of dimethylformamide per hour per liter of reactor, only 1.17% of sodium methoxide is used in the process of the present invention when operating at 70° C. and at 20 bars, whereas in the process of British Patent Specification No. 1,213,173, in order to achieve this productivity, it is necessary to use 1.50% of sodium methoxide and to operate at 120° C. and at 50 bars.

EXAMPLE 5.

The procedure of Example 1 is followed, but 31.8 kg. of a mixture containing 69.76% by weight of dimethylamine, 29.79% by weight of methanol and 0.45% by weight of sodium methoxide (0.65% by weight referred to the dimethylamine) and also 17.2 kg. of carbon monoxide of 99.5% purity are introduced per hour. The temperature is 70° C. and the pressure 22 bars.

48.2 kg. of a mixture containing 74.68% by weight of dimethylformamide and 11.45% by weight of methyl formate are withdrawn per hour at D. The production of (100%) dimethylformamide is, therefore, 36 kg. per hour and that of (100%) methyl formate 5.5 kg. per hour. The productivities in respect of dimethylformamide and methyl formate are, therefore, respectively, 0.6 and 0.09 kg. per hour per liter of reactor. The yield referred to carbon monoxide is 95 mol percent and the conversion of dimethylamine is 100%.

This Example shows that dimethylformamide and methyl formate can be produced simultaneously. The productivity of dimethylformamide is obviously lower in this case, although still higher than that obtained in the prior art process (0.6 as against 0.43).

EXAMPLE 6.

As in Example 1, 32.7 kg. of a mixture containing 97.56% by weight of dimethylamine, 1.71% by weight of methanol and 0.73% by weight of sodium methoxide (0.75% by weight referred to the dimethylamine) and also 31.89 kg. of carbon monoxide of 99.5% purity are introduced per hour.

52.14 kg. of a mixture containing 97.2% by weight of dimethylformamide are withdrawn per hour at D, i.e. 50.7 kg. per hour of 100% product.

The productivity is 0.84 kg. of dimethylformamide per hour per liter of reactor.

This Example shows that it is also possible to carry out the process of the present invention with a relatively very small amount of methanol. Under these conditions, a precipitate of sodium methoxide may be formed but this does not in any way impair the synthesis in view of the intensive, tumultuous circulation of the reaction mixture through the apparatus. This precipitate is not deposited on the surfaces, including the heat exchange surface, as can easily be seen from the fact that the reaction temperature is kept constant at 90° C.

EXAMPLE 7.

The process is exactly the same as in Example 1 except that a gaseous mixture containing about 50% of carbon monoxide and about 50% of hydrogen is introduced and that a total pressure of 100 bars is maintained (i.e. a partial pressure of carbon monoxide of about 20 bars), taking into account the blow-off at 7.

The same productivity of dimethylformamide is observed as in Example 1 (about 2 kg. of methylformamide per hour per liter of reactor), but the yield referred to carbon monoxide is now only 75 mol percent.

EXAMPLE 8.

The procedure of Example 1 is followed, but a mixture containing 71.58% of ammonia, 27.52% of methanol and 0.9% of sodium methoxide (1.26% referred to the ammonia) is introduced at the rate of 107.8 kg. per hour.

41.3 kg. of carbon monoxide of 99.5% purity is introduced per hour at 5.

The pressure is kept at 75 bars and the temperature at 90° C. (the partial pressure of ammonia at this temperature is about 35 bars).

The yield referred to carbon monoxide is 95 mol percent, while the conversion of ammonia to formamide is about 50%. The unconverted ammonia is returned to the feed, together with the methanol, and the ammonia content of the mixture introduced is made up by adding about 50% of fresh ammonia.

In order to keep the level constant at 11, 105.7 kg. of a mixture containing 59.6% of formamide is withdrawn per hour at D, i.e. a production of 63 kg. of formamide per hour. Therefore, productivity is 1,05 kg. of formamide per hour per liter of reactor.

EXAMPLE 9.

The procedure of Example 1 is followed, but 87.05 kg. of a mixture containing 69.62% by weight of monomethylamine, 29.87% by weight of methanol and 0.5% by weight of sodium methoxide (0.45% referred to the monomethylamine) and also 56.5 kg. of carbon monoxide of 99.5% purity are introduced per hour. The temperature is fixed at 90° C. and the pressure at 25 bars.

140.75 kg. of a mixture containing 80.5% by weight of monomethylformamide are withdrawn per hour at D, i.e. a production of 113.4 kg. of monomethylformamide per hour and a productivity of 1.89 kg. monomethylformamide per hour per liter of reactor.

We claim:

1. In a process for the production of a formamide, wherein a current of a gas containing carbon monoxide is reacted at elevated temperature and pressure in a reaction zone with a recycled current of liquid reaction mixture containing
   (a) a nitrogen-containing compound selected from the group consisting of ammonia, a primary alkylamine and a secondary alkylamine,
   (b) a methanolic solution of an alkali metal or alkaline earth metal methoxide as catalyst, and
   (c) the formamide produced as reaction product,
part of the current of liquid reaction mixture being withdrawn in order to recover the formamide therefrom, the improvement which comprises using the recycled current of liquid reaction mixture for sucking and dispersing the current of gas in the reaction zone.

2. A process according to claim 1, wherein the temperature in the reaction zone is from about 50° to about 200° C.

3. A process according to claim 1, wherein the temperature in the reaction zone is from about 60° to about 100° C.

4. A process according to claim 1, wherein the pressure in the reaction zone is from 5 to 110 bars.

5. A process according to claim 1, wherein the pressure in the reaction zone is from 10 to 25 bars.

6. A process according to claim 1, wherein the alkylamine is an alkylamine the alkyl radical or radicals of which contains 1 or 2 carbon atoms.

7. A process according to claim 1, wherein the alkylamine is a methylamine.

8. A process according to claim 1, wherein the molar ratio of carbon monoxide to the nitrogen-containing compound is from 0,2 to 2,0.

9. A process according to claim 1, wherein the molar ratio of carbon monoxide to the nitrogen-containing compound is from 0,2 to 1,4.

10. A process according to claim 1, wherein the catalyst is used in an amount of from about 0,2 to about 4,0% by weight, referred to the amount of nitrogen-containing compound used.

11. A process according to claim 1, wherein the catalyst is used in an amount of from about 0,4 to about 2,5% by weight, referred to the amount of nitrogen-containing compound used.

12. A process according to claim 1, wherein the catalyst is sodium methoxide.

13. A process according to claim 1, wherein the surface contact area between the gas phase and the liquid phase is of from 750 to 5,000 sq.meters per cubic meter of liquid phase.

14. A process according to claim 1, wherein the surface contact area between the gas phase and the liquid phase is of from 1,000 to 2,000 s.q.meters per cubic meter of the liquid phase.

15. A process according to claim 1, wherein the gas containing carbon monoxide is substantially pure carbon monoxide.

16. A process according to claim 1, wherein the gas containing carbon monoxide is a mixture containing about 50% of carbon monoxide and about 50% of hydrogen.

* * * * *